(12) United States Patent
Fewster et al.

(10) Patent No.: US 6,731,719 B2
(45) Date of Patent: May 4, 2004

(54) X-RAY DIFFRACTOMETER

(75) Inventors: Paul F. Fewster, Brighton (GB); Norman L. Andrew, Crawley (GB)

(73) Assignee: PANalytical B.V., Ea Almelo (NL)

( * ) Notice: Subject to any disclaimer, the term of this patent is extended or adjusted under 35 U.S.C. 154(b) by 0 days.

(21) Appl. No.: 10/022,150

(22) Filed: Dec. 13, 2001

(65) Prior Publication Data

US 2002/0075995 A1 Jun. 20, 2002

(30) Foreign Application Priority Data

Dec. 20, 2000 (GB) .............................. 0031040

(51) Int. Cl.$^7$ ............................................ G01N 23/207
(52) U.S. Cl. ................... 378/71; 378/79; 378/84
(58) Field of Search .......................... 378/70, 71, 72, 378/73, 75, 76, 81, 82, 84

(56) References Cited

U.S. PATENT DOCUMENTS

| | | | |
|---|---|---|---|
| 5,850,425 A | 12/1998 | Wilkins | 378/85 |
| 5,878,106 A * | 3/1999 | Fujiwara | 378/79 |
| 6,226,349 B1 * | 5/2001 | Schuster et al. | 378/84 |

FOREIGN PATENT DOCUMENTS

| | | | |
|---|---|---|---|
| EP | 0318012 A 2 | 5/1989 | G01N/23/207 |
| JP | A01270650 | 10/1989 | G01N/23/207 |
| JP | A001276052 | 11/1989 | G01N/23/207 |

OTHER PUBLICATIONS

B. D. Cullity. Elements of X–Ray Diffraction, second edition (Reading, MA: Addison–Wesley, 1978), pp. 188–196, 156–158.*

"Characterization of Thin Layers on Perfect Crystals with a Multipurpose High Resolution X–ray Diffractometer", Bartels, Journal Vacuum Science and Technology B vol. 1 p. 338 (1983).

* cited by examiner

Primary Examiner—Edward J. Glick
Assistant Examiner—Allen C. Ho
(74) Attorney, Agent, or Firm—Blakely, Sokoloff, Taylor & Zafman

(57) ABSTRACT

An X-ray diffractometer has an X-ray source (10), a double pinhole collimator (14), a sample (22) mounted on a rotatable sample stage (20), an analyser crystal (30) and a detector (34). The analyser crystal and detector are arranged to rotate together about an axis (21) that is coaxial with the axis of rotation of the sample stage. Very few scattered X-rays (26) reach the detector (34). The diffractometer has particular use for routine quality control measurements.

3 Claims, 6 Drawing Sheets

X-RAY DIFFRACTOMETER

FIELD OF THE INVENTION

The invention relates to an X-ray diffractometer.

BACKGROUND OF THE INVENTION

X-ray diffractometers have been used for many years for analysing perfect, nearly perfect and highly imperfect materials on a routine basis.

An early high resolution diffractometer is the double-crystal diffractometer which is illustrated in FIG. 1. An X-ray source 1 transmits X-rays to a collimating crystal 3 which directs them onto a sample 5 which can be rotated about an axis 7. The X-rays are diffracted by the sample 5 onto a detector 9. The sample is then rotated and the intensity of X-rays reaching the detector is measured as a function of the angle of this rotation. This structure is still widely used, and gives good results especially on perfect and near-perfect samples.

Unfortunately, double crystal diffractometers have a number of disadvantages. Firstly, the Bragg angle of the collimating crystal 3 has to match that of the sample 5. The matching of the collimating crystal and the sample crystal is very important and the resolution is fixed by the crystals. Accordingly, a different collimating crystal 3 is required for each new sample material.

Secondly, the X-rays in a double crystal diffractometer reach a large and ill-defined region of the sample. Since this ill-defined region is the region analysed, X-ray diffractometers do not give good results for non crystalline materials or materials with defects.

Thirdly, in a double crystal diffractometer a number of different wavelengths are diffracted into the detector simultaneously. This reduces the precision and resolution of the results.

Fourthly, there is a large background level of illumination that reaches the detector from imperfect samples which makes analysis of any results a problem.

Furthermore, the double crystal diffractometer is very sensitive to the alignment and significant changes can be observed with a tilt angle varying by only 0.2°. This makes the double crystal diffractometer difficult to set up.

A number of proposals to alleviate some of these problems have been made.

Bartels describes a diffractometer which removes the inconvenience of having to change the crystal in "Characterization of Thin Layers on Perfect Crystals with a Multipurpose High Resolution X-ray Diffractometer", Bartels, Journal Vacuum Science and Technology B Volume 1 page 338 (1983). Bartels replaced the collimating crystal of a double crystal diffractometer with two channel-cut monochromators which provide a good monochromator with a very narrow angular divergence. However, this change to the double-crystal diffractometer geometry does not solve many of the problems of the double-crystal diffractometer. In particular, the Bartels diffractometer cannot be used for interpreting complex diffraction patterns from all but the most perfect and flat samples.

Another prior art design is a triple-crystal diffractometer which overcomes the problem of a bent sample and produces a significantly improved diffraction profile. This is illustrated in FIG. 2. The triple crystal diffractometer differs from the double crystal diffractometer by having a further analysing crystal 4 interposed between the sample 5 and the detector 9. Each of the crystals is independently rotatable. The analyser acts as a detector with a very narrow angular acceptance.

Unfortunately, away from the position in which all three crystals have the same scattering angle the recorded intensity profile recorded at the detector broadens rapidly. Furthermore, alignment is very difficult and this configuration has accordingly only been used by a few research groups. Moreover, each new sample still requires a new collimating crystal.

The current state of the art commercial instrument is a multiple crystal diffractometer, in which the collimating crystal 3 of the triple crystal diffractometer is replaced by a multiple crystal collimating arrangement.

Commercial diffractometers may be used in particular for quality control. In practice it is the double crystal approach that has traditionally been used, and the very difficult alignment of the triple-axis diffractometer is normally avoided. Although the multiple crystal diffractometer is an excellent research instrument, it has not replaced the simpler double crystal diffractometer for production line control. In view of the disadvantages of the double crystal configuration mentioned above there is a need for an alternative X-ray diffractometer suitable for routine use that addresses these disadvantages.

SUMMARY OF THE INVENTION

According to the invention there is provided an X-ray diffractometer, comprising a sample stage for mounting a sample, the sample stage being rotatable about an axis, a double pinhole collimator for directing X-ray radiation to a sample on the sample stage, a detector for detecting X-rays diffracted by the sample, and an analyser crystal arranged between the sample stage and the detector to direct X-rays diffracted by the sample onto the detector, wherein the analyser crystal and detector are rotatable about an axis that is coaxial with the axis of rotation of the sample stage.

The new instrument reverses the crystals of a conventional double crystal arrangement and provides the second crystal after the sample rather than before. This gives greater precision in the measurement of the scattered beam direction which is most crucial for coping with imperfect materials. Moreover, the arrangement removes the need for precise wavelength control of the probing beam, which is why it is possible to replace the collimating crystal of a triple-axis arrangement with a double pinhole collimator.

As will be apparent from experimental results presented later, the diffractometer according to the inventor produces results approaching, possibly in some cases even surpassing, those obtained using a multiple crystal diffractometer. This is in spite of the fact that the diffractometer according to the invention is very much simpler to set up and to use.

The analysed region of the sample is much better defined and smaller in the diffractometer according to the invention than in a conventional double crystal diffractometer. This is because the sample is placed after the pinhole collimator. This produces a spot on a sample mounted on the sample stage with a well-defined central region (the umbra) and very little X-ray intensity in the penumbra (the region surrounding the umbra). To obtain a well defined and small region using a conventional double crystal diffractometer would require either a smaller spot area or alternatively complex focusing optics. These are not required in the diffractometer according to the invention.

A further difference over a conventional double crystal diffractometer is the narrow angular acceptance of the analyser, i.e. the analyser crystal can be nearly perfect and can direct into the detector X-rays only in a narrow angular range around the correct angle of incidence.

A significant advantage of the invention is that the combination of a well defined analysed region of the sample and the narrow angular acceptance of the analyser can greatly reduce the background and diffuse scattering that can easily make analysis a problem using a conventional double crystal diffractometer. Such scatter might frequently in prior art arrangements be X-rays diffracted from imperfect regions of the sample or from X-rays diffracted along paths not of interest to the analysis. Similarly the curvature of the sample will have a smaller influence on the breadth of the recorded intensity profile because of the narrow double pinhole collimator and analyser crystal.

In particular the combination of the well defined small analysed region and the narrow angular acceptance of the analyser crystal and detector greatly improves the performance with imperfect samples. In such imperfect sample small mosaic block sizes, defects, microscopic tilts and curvature can make it very difficult to analysis any data obtained with a conventional double crystal diffractometer. Whilst a triple axis diffractometer can significantly improve the resolution such triple axis diffractometers are extremely difficult to set up and therefore less suited to fast and routine analysis for quality control applications.

The measurement of the scattering angle is very robust. Even moving the sample out with respect to the sample stage so that the sample is one millimeter away from the optimal position gave a reproducibility of 0.0001° in the measured scattering angle on a 004 reflection of a high quality silicon sample. Even with such a grossly misaligned sample the value of the lattice perimeter was measured to be 5.43104 Å which is within 1.8 ppm of the accepted value. Measurement of a slightly damaged piece of silicon gave a measurably different value of 5.43113 Å.

A further benefit of the invention is that the diffractometer is not particularly sensitive to alignment. Tilting the sample does not give rise to significant loss of quality. This occurs because the analysing crystal can be precisely aligned and the X-rays hitting the sample are less precisely aligned than when using a collimating crystal and so the analysis is less sensitive to inaccuracies in alignment. Thus, in many cases experiments may be carried out without any tilt alignment.

The insensitivity of the diffractometer according to the invention both to tilt angle and to exact sample alignment makes the diffractometer easier to use, and hence can speed up analysis.

The analyser crystal and detector are preferably rotatable about an axis that is coaxial with the axis of rotation of the sample stage. The measured analyser angle is then the true scattering angle.

The use of the analyser crystal also significantly improves dispersive effects caused by the plurality of wavelengths in the X-ray source. This means that the same analyser crystal can be used for a whole range of experiments. This is not possible with a conventional double crystal diffractometer since the sample axis is rotated and all wavelengths that are scattered from the collimating crystal may arrive at the detector.

If the discrimination is required to be improved a small slit may be placed in front of the analyser crystal or in front of the detector. By placing the discrimination far from the source in this way a larger separation of angles for different wavelengths is obtained which makes it much easier to discriminate between those different wavelengths than would be possible in prior approaches.

The pinhole size may be adjustable which allows the resolution to be changed depending on the sample. This change in pinhole size can also allow the adjustment of the area of the sample analysed. A small spot size can allow the resolution to be roughly good as with a multiple crystal diffractometer configuration. Larger spot sizes can increase x-ray intensity and hence measurement speeds. Such adjustment is particularly useful for quality control of discrete devices.

The X-ray diffractometer may further include a drive to rotate the sample stage and the analyser crystal and detector in a 1:2 ratio. Each stage may be separately driven under computer control.

In another aspect there is provided a method of X-ray diffractometery, comprising
    directing X-rays through a double pinhole collimator onto a sample to be measured,
    diffracting the X-rays diffracted by the sample from an analyser crystal onto a detector,
    rotating the sample and rotating the analyser crystal and detector about coaxial axes, and
    measuring the diffracted X-ray intensity as a function of the angle of rotation of the sample and the angle of rotation of the analyser crystal and detector.

The method may include varying the size of at least one pinhole in the double pinhole collimator.

It is possible to measure the scattering angle to within 0.0001° but it is inconvenient to have to align a sample on the sample stage to this very high level of accuracy. Accordingly, the method may include the steps of
    mounting the sample on a sample stage;
    rotating the analyser crystal and detector to a predetermined position;
    rotating the sample whilst keeping the analyser crystal and detector in the predetermined position and measuring the X-rays reaching the detector as a function of angle of sample rotation; and
    determining the sample rotation angle at which the measured X-rays are at a peak and rotating the sample to that angle.

In this way the sample can be mounted on the stage without needing accurate alignment and the sample can then be aligned by rotating the sample to the angle wherein an X-ray peak is measured, without having to align the sample to the sample stage with extreme accuracy.

The method may further comprise the step of rotating the sample and the analyser crystal and detector with rotation speeds substantially in a 1:2 ratio.

BRIEF DESCRIPTION OF THE DRAWINGS

For a better understanding of the invention, specific embodiments will now be described, purely by way of example, with reference to the accompanying drawings in which.

DETAILED DESCRIPTION OF THE INVENTION

Figure 1:
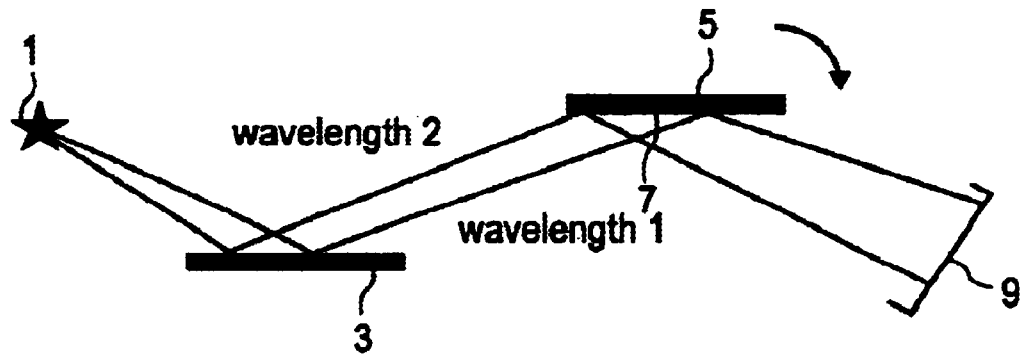
FIG. 1 shows a conventional double-crystal diffractometer configuration.
Figure 2:
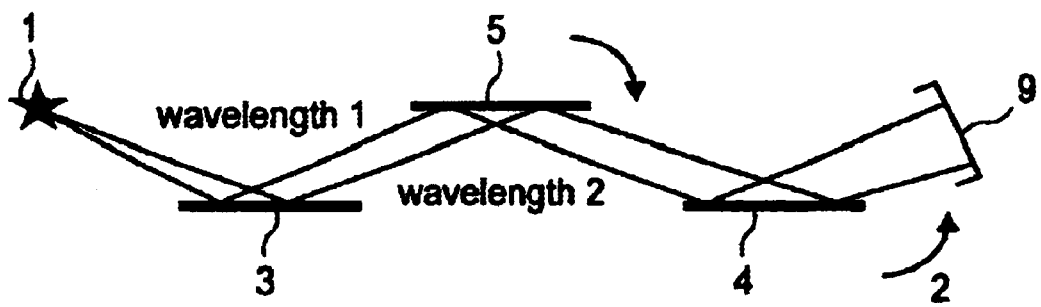
FIG. 2 shows a conventional triple-axis diffractometer.
Figure 3:
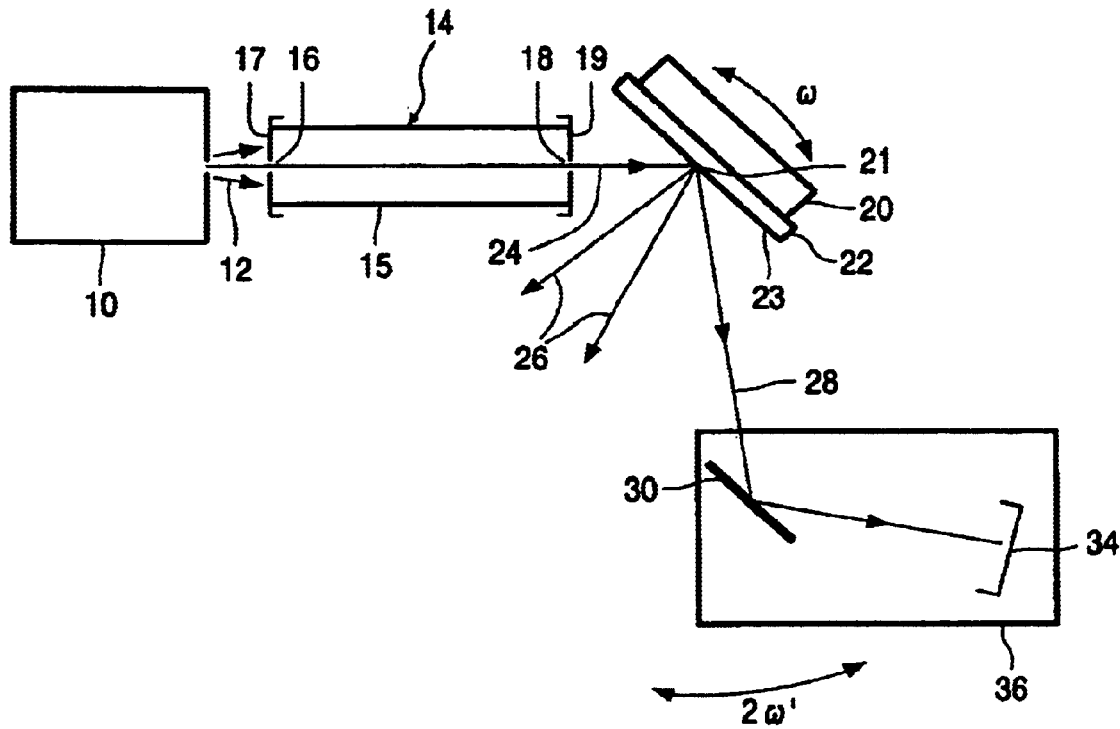
FIG. 3 shows a schematic drawing of an embodiment of the invention.

A diffractometer according to a first embodiment of the invention has an X-ray source 10 which produces CuKα X-rays. It will be appreciated that any suitable X-ray line for diffractometery may be used, and that the source may be any suitable source of X-rays, such as a cathode type X-ray apparatus or a synchrotron. The X-ray source emits X-rays 12 towards a double pinhole collimator 14 having a hollow body 15 with first 16 and second 18 pinholes arranged at opposed ends of the hollow body 15. The first pinhole second pinholes 18 are small substantially circular holes of variable diameter (0.2 mm to 1 mm). This may be achieved in any known way, most simply by providing interchangeable removable end sections 17, 19 defining the pinholes 16, 18, so that the diameter can be varied simply by replacing an end section having a pinhole of one diameter with an end section having a pinhole of another diameter.

A sample stage 20 rotatable about an axis 21 for mounting a sample 22 is provided. The axis of rotation of the stage is arranged so that the axis passes through the front face 23 of the sample facing the X-ray source. An analyser crystal 30 is arranged on a detector 34. The analyser crystal and detector are both arranged on a detection stage 36 which is mounted to rotate the analyser and detector about an axis that is co-axial with the axis of rotation of the sample stage. The analyser crystal is a high-quality crystal with known diffraction properties that produces little background scattering.

The sample stage and detector stage are independently rotatable. In use, a sample 22 is mounted on the sample stage 20. X-rays 12 are collimated into a beam 24 by the double pinhole collimator and illuminate a small spot on the sample. Scattered X-rays 26 are not collected. Diffracted X-rays 28 are incident on the analyser crystal 30 and diffracted by the analyser crystal 30 onto the detector 34. The detection stage 36 and the sample stage 20 are rotated and the intensity of X-rays reaching the detector is measured as a function of rotation angle.

The diffractometer according to the invention may be set up as follows. The detector stage 36 is arranged so that X-rays passing through the collimator impact the analyser crystal. The analyser crystal 30 is approximately rotated to reflect the direct beam into the detector. A scan rotating the detector stage 36 about its axis 21 is then performed to locate the position of maximum intensity, i.e. the zero point of no scattering.

A sample 22 is then mounted on the sample stage 20 at the axis 21 to within a tolerance of a few mm. Tilt alignment of the sample is rarely necessary.

The detector stage is placed at a predetermined scattering angle.

The sample stage alone is then rotated until the maximum substrate scattering is measured by the detector. The sample stage is then rotated to this position and the sample and detector stages coupled together.

The sample and detector states are then rotated with a 1:2 ratio, i.e. the sample is rotate by half the angle of the detector stage. This keeps the detector at the correct angle to receive diffracted X-rays.

The detector measures the X-ray intensity which is recorded as a function of the sample rotation angle ω.

The pinholes are arranged at a distance of about 10 mm to 130 mm from the sample stage 20. It will be appreciated that this distance can be varied. However, the closer the pinholes are to the sample the better the definition of the spot. For a pinhole close to the sample, at 10 mm distance, the spot of X-rays on the sample has almost all the intensity concentrated in a central region, the umbra, and very little intensity in the tail, the penumbra. At longer distances the size of the penumbra and the total intensity of X-rays in the penumbra increases.

Figure 4:
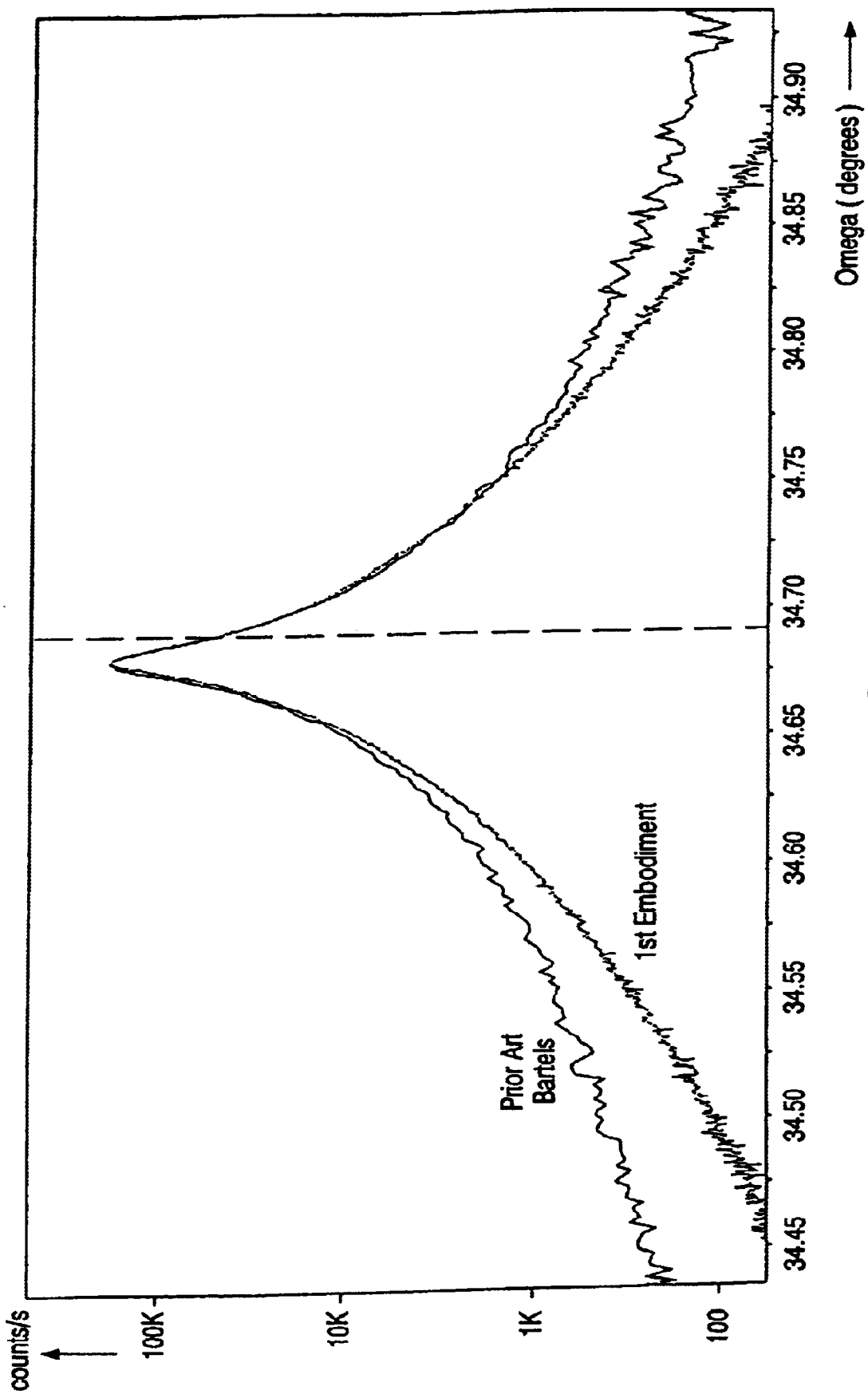
FIG. 4 shows a comparison between the diffraction peak obtained with a diffractometer according to the invention and with a Bartels monochromator.

FIG. 4 compares the diffraction peak recorded as a function of angle using a diffractometer according to the invention having two 1 mm pinholes and using a Bartels configuration improved by using two crossed slits in the X-ray path. The diffraction peak measured using the invention is clearly narrower and better defined.

Figure 5:
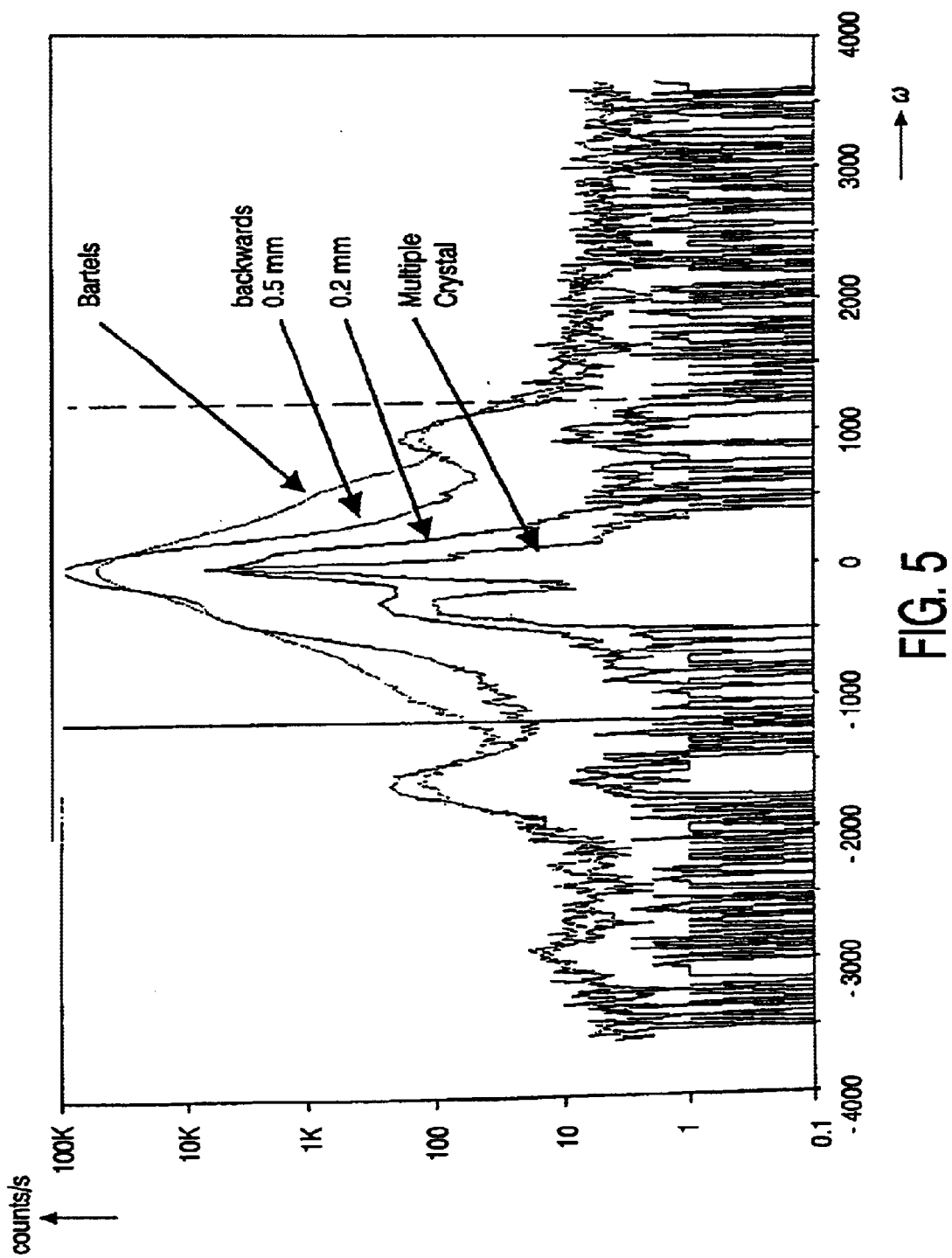
FIG. 5 shows a comparison between a Bartels configuration, a multiple crystal axis configuration and two diffractometers in accordance with the invention with a variable pinhole size.

FIG. 5 is a graph of the diffraction peak of a highly imperfect sample of GaN obtained with a Bartels configuration, with a multiple crystal diffractometer and a diffractometer according to the invention with 0.5 mm and 0.2 mm pinholes. As can be seen, the resolution obtained with the invention approaches that obtained using a multiple crystal diffractometer without all the inconvenience associated with such a diffractometer. It is surprising that the invention produces such good results in a system that is very much simpler than the multiple crystal approach.

Excellent results were also obtained whilst measuring an InGaAs/GaAs single quantum well laser, with a diffractometer according to the first embodiment having 1 mm, 0.5 mm and 0.2 mm pinholes and for comparison a Bartels arrangement and a multiple crystal arrangement. The diffractometer according to the invention can obtain a better resolution, when using a small pinhole, than either of two prior art approaches, the Bartels approach and the multiple crystal diffractometer. It is surprising that such good results can be obtained in a system that is so simple to use.

Figure 6:
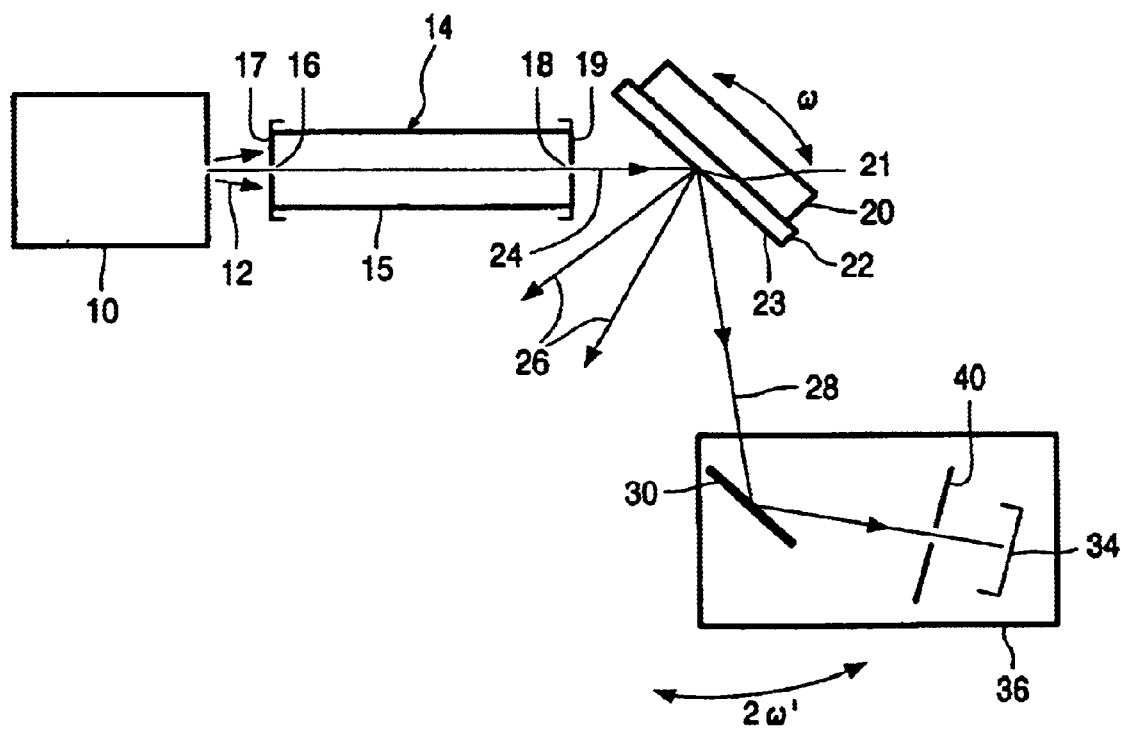
FIG. 6 illustrates a second embodiment of the invention having a slit in front of the detector.
Figure 7:
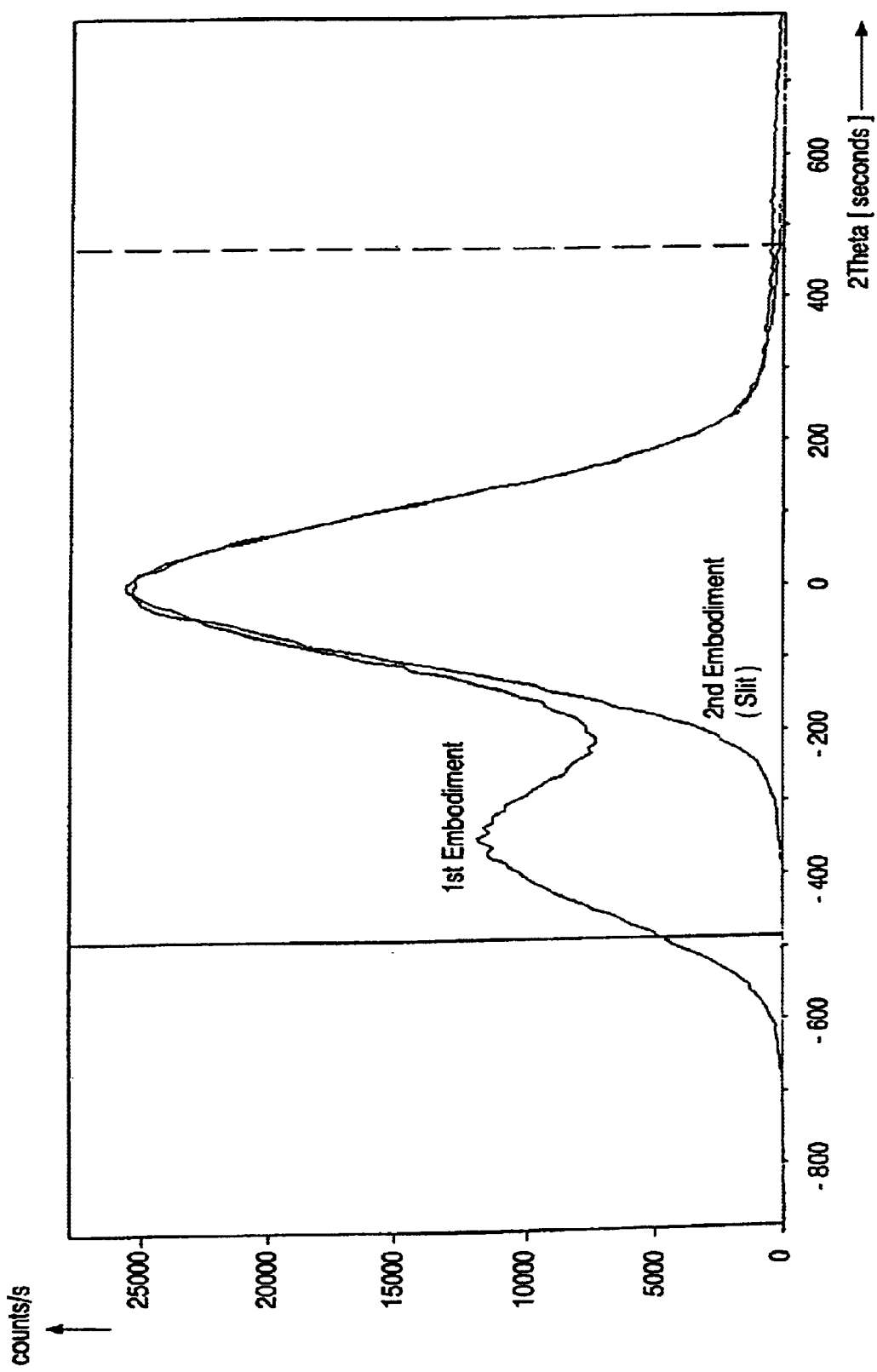
FIG. 7 illustrates the removal of the CuK$\alpha_2$ peak in a diffractometer according to the second embodiment.

In a second embodiment of the invention, a 1 mm slit 40 was placed in front of the detector 34 as shown in FIG. 6. Again, 1 mm diameter pinholes are used. FIG. 7 illustrates measurements with and without the slit. The graph clearly shows the double peak caused by the fact that the emission line used, CuKα, is in fact a doublet. However, in the graph using a slit in front of the detector the component from one of the doublet pair is removed, in spite of the very similar wavelengths of the pair. This improvement in the wavelength discrimination can narrow the measured peaks by avoiding the dual peaks of the first embodiment.

Figure 8B:
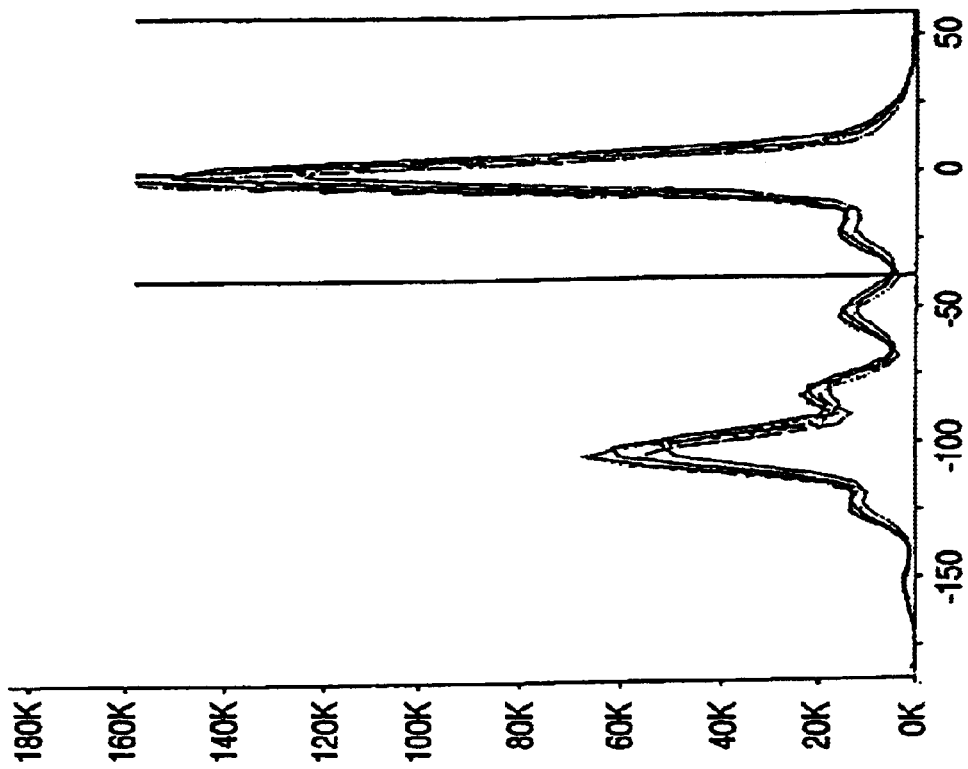
FIG. 8b illustrates results obtained whilst determining the composition of a Quantum Well Laser.
Figure 8A:
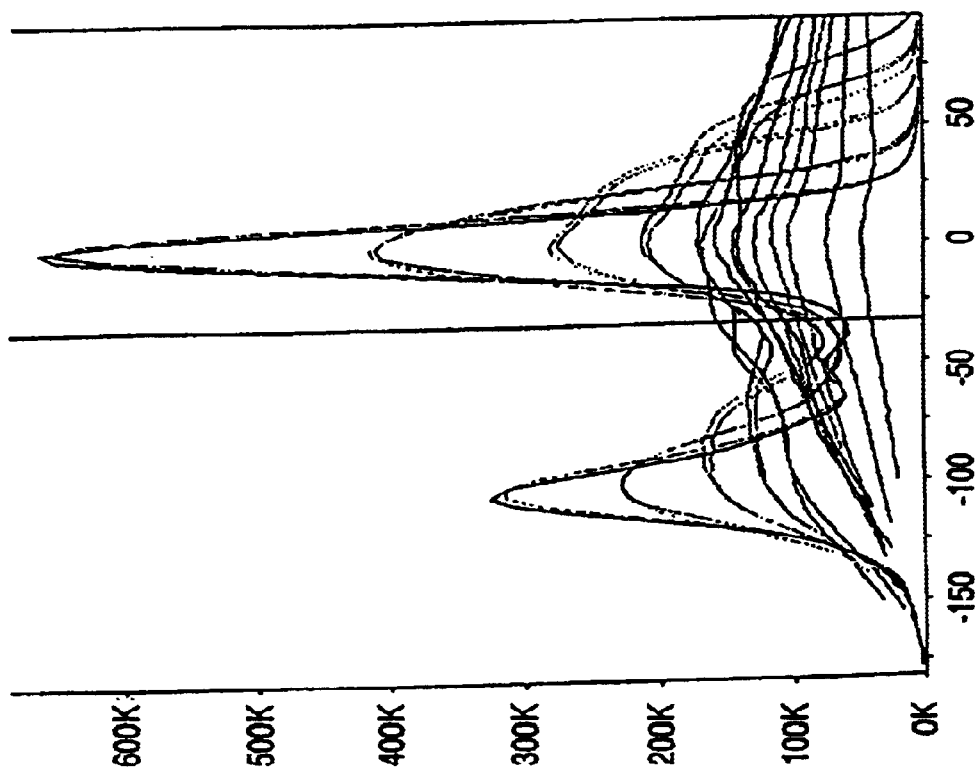
FIG. 8a illustrates the insensitivity of the diffractometer according to the invention to tilt.

FIG. 8b shows the diffraction pattern obtained using a diffractometer according to the invention having 0.5 mm pinholes at several different tilt angles at 0.20° intervals over a 40° range. For comparison, the diffraction pattern using the Bartels configuration at the same tilt angles is also shown in FIG. 8a. The graph using the Bartels configuration is highly sensitive to tilt and a great variation is observed. In contrast, there is very little difference between the graphs taken using the diffractometer according to the invention at different tilt angles.

The insensitivity of the diffractometer to tilt alignment speeds set up and alignment of the diffractometer.

Although the invention has been described with reference to the specific embodiment above it will be appreciated that there are many alternatives to the embodiment described.

What is claimed is:

1. A method of X-ray diffractometery, comprising the stops of:

mounting the sample on a sample state;

directing X-rays through a double pinhole collimator onto a sample to be measured;

diffracting the X-rays diffracted by the sample with an analyser crystal onto a detector;

rotating the sample and rotating the analyser crystal and the detector about coaxial axes;

measuring the diffracted X-ray intensity as a function of the angle of rotation of the sample and the angle of rotation of the analyser crystal and detector;

rotating the analyser crystal and detector to a predetermined position;

rotating the sample whilst keeping the analyser crystal and detector in the predetermined position and measuring the X-rays reaching the detector as a function of angle of sample rotation;

determining the sample rotation angle at which the measured X-rays are at a peak and rotating the sample to that angle; and rotating the sample and the analyser crystal and detector about coaxial axes; and measuring the diffracted X-ray intensity as a function of rotation angle of the sample and the angle of rotation of the analyzer crystal and detector.

2. A method of X-ray diffractometery according to claim 1 and further including varying the size of at least one pinhole in the double pinhole collimator.

3. A method of X-ray diffractometery according to claim 1 and further comprising the step of:

rotating the sample and the analyser crystal and detector with rotation speeds substantially in a 1:2 ratio.

* * * * *